United States Patent
Tamagawa et al.

(10) Patent No.: US 7,708,725 B2
(45) Date of Patent: May 4, 2010

(54) SANITARY NAPKIN

(75) Inventors: Noritatsu Tamagawa, Kagawa (JP);
Masataka Kinoshita, Kagawa (JP);
Kazuya Nishitani, Kagawa (JP);
Toshiyuki Tanio, Kagawa (JP)

(73) Assignee: Uni-Sharm Corporation, Ehime (JP)

( * ) Notice: Subject to any disclaimer, the term of this patent is extended or adjusted under 35 U.S.C. 154(b) by 385 days.

(21) Appl. No.: 10/862,928

(22) Filed: Jun. 7, 2004

(65) Prior Publication Data

US 2004/0260263 A1    Dec. 23, 2004

(30) Foreign Application Priority Data

Jun. 20, 2003    (JP) .............................. 2003-177363

(51) Int. Cl.
*A61F 13/15* (2006.01)

(52) U.S. Cl. ........... 604/385.04; 604/380; 604/385.101; 604/385.28

(58) Field of Classification Search ................................
604/385.04–385.05, 385.25–385.28, 385.101, 604/380
See application file for complete search history.

(56) References Cited

U.S. PATENT DOCUMENTS

| | | | | |
|---|---|---|---|---|
| 5,704,928 | A * | 1/1998 | Morita et al. ........... | 604/385.23 |
| 5,820,618 | A * | 10/1998 | Roberts et al. .......... | 604/385.04 |
| 6,375,645 | B1 * | 4/2002 | Nishida et al. .......... | 604/385.02 |
| 6,497,688 | B2 * | 12/2002 | Lasko ......................... | 604/367 |
| 6,508,796 | B2 | 1/2003 | Mizutani et al. | |
| 6,517,525 | B1 * | 2/2003 | Berthou et al. ......... | 604/385.101 |
| 6,569,140 | B1 | 5/2003 | Mizutani et al. | |
| 7,056,311 | B2 * | 6/2006 | Kinoshita et al. ...... | 604/385.04 |
| 2007/0055212 | A1 * | 3/2007 | Kameo et al. ........... | 604/385.04 |

FOREIGN PATENT DOCUMENTS

| | | |
|---|---|---|
| JP | 7-33314 | 6/1995 |
| JP | 10-75975 | 3/1998 |
| JP | 2001-095842 | 4/2001 |
| JP | 2001-095844 A1 | 4/2001 |

OTHER PUBLICATIONS

Kinoshita et al., U.S. Appl. No. 10/841,363, "Sanitary Napkin", May 7, 2004.
Tanio, et al., U.S. Appl. No. 10/847,823, "Absorbent Article", May 17, 2004.
Nishitani et al., U.S. Appl. No. 10/862,926, "Sanitary Napkin", Jun. 7, 2004.

* cited by examiner

*Primary Examiner*—Tatyana Zalukaeva
*Assistant Examiner*—Lynne Anderson
(74) *Attorney, Agent, or Firm*—Darby & Darby P.C.

(57) ABSTRACT

A sanitary napkin that is provided with large rear flaps to effectively prevent liquid from leaking obliquely rearward. The rear flaps are disposed rearward of fold-back flaps to be wrapped around a crotch part of an undergarment. The rear flap is of a shape spreading rearwardly from a starting point. With a pressure from the thighs acting forward of the starting point, leakage preventing walls forward of the starting point can be maintained in a rising state during wear. On the other hand, the leakage preventing walls rearward of the starting point may possibly fall outward. However, even if the leakage preventing walls fall outward rearward of the starting point, they will never project out of the rear flaps. Accordingly, they hardly leave a stain on an undergarment.

11 Claims, 6 Drawing Sheets

SANITARY NAPKIN

BACKGROUND OF THE INVENTION

1. Field of the Invention

The present invention relates to a sanitary napkin suitable for nighttime use. More particularly, the invention relates to a sanitary napkin provided with rear flaps for widely covering a posterior part of the crotch and the buttocks.

2. Description of the Related Art

For nighttime use, there have been known elongated sanitary napkins with fold-back flaps in its front portion and rear flaps in its rear portion.

FIG. 8 is a top plan view showing a conventional sanitary napkin 101 of this type with its skin-side surface directed upward.

The sanitary napkin 101 has a main body constructed to include: a liquid-permeable topsheet located on the skin-side surface; a liquid-impermeable backsheet located on the garment-side surface; and a liquid absorbent layer disposed between the topsheet and the backsheet. The main body has a front portion with fold-back flaps 102, 102 projecting from transversely opposing sides thereof and a rear portion with rear flaps 103, 103 projecting from the transversely opposing sides. The sanitary napkin 101 is intended to be placed on an inner surface of an undergarment from a crotch part to a back body and fixed to the inner surface of the undergarment through a pressure-sensitive adhesive layer disposed on a garment-side surface of the backsheet.

The fold-back flaps 102, 102 may be folded back to cover either side edge of the crotch part of the undergarment and adhered to an outer surface of the crotch part through pressure-sensitive adhesive layers. The rear flaps 103, 103 may be placed on the undergarment in an unfolded state to extend from a rear portion of the crotch part to the back body, wherein the garment-side surfaces of the rear flaps 103, 103 can be fixed to the inner surface of the undergarment through pressure-sensitive adhesive layers.

On the skin-side surface of the main body, leakage preventing walls 104, 104 are provided to extend longitudinally on each side of a longitudinal centerline Oy-Oy. Each leakage preventing wall 104 is provided with longitudinally extending elastic members for exerting an elastic contractive force between front and rear ends 105, 106. With the elastic contractive force, the leakage preventing wall 104 is raised from the skin-side surface between the front and rear ends 105, 106.

In the sanitary napkin 101, a front region 107a between the fold-back flaps 102, 102 is intended to face the vaginal opening, and an intermediate region 107b is intended to face the perineum and the anus. In a rear region 107c, the sanitary napkin is deformed to rise along the longitudinal centerline Oy-Oy for fit in the cleft of the buttocks.

Sanitary napkins of this type are disclosed, for example, in the following Patent Publications 1 and 2. In the sanitary napkin disclosed in the Patent Publication 1, since the rear ends 106, 106 of the leakage preventing walls 104, 104 are located farther rearward than shown in FIG. 8, menstrual blood discharged from the vaginal opening and trying to flow obliquely rearward may be blocked.

[Patent Publication 1]
Japanese Unexamined Patent Publication No. 2001-95842

[Patent Publication 2]
Japanese Unexamined Patent Publication No. H07-33314

When the undergarment is worn with the sanitary napkin 101 of FIG. 8 being adhered and fixed thereto, the inside of the wearer's thigh faces a region extending over a length of 150 to 170 mm with center at a transverse reference line Ox-Ox of the sanitary napkin 101. Since the thighs exert a transverse clamping force on this region, the leakage preventing walls 104, 104 come into contact with the thighs, hardly falling transversely outward.

Rearward of a line Lx-Lx that is spaced 70-80 mm apart rearwardly from the transverse reference line Ox-Ox, however, the leakage preventing walls 104, 104 cannot come into contact with the thighs. Rearward of the line Lx-Lx, moreover, the leakage preventing walls 104, 104 will be subjected to a pressure from the buttocks. Therefore, the leakage preventing walls 104, 104 rearward of the line Lx-Lx tend to fall outward without being constrained by the thighs.

In the conventional sanitary napkin 101 of FIG. 8, the rear flaps 103, 103 have side edges 103a, 103a that are located close to the leakage preventing walls 104, 104 on the line Lx-Lx. When the leakage preventing walls 104, 104 fall transversely outward, therefore, they extend beyond the side edges 103a, 103a, so that menstrual blood applied to the leakage preventing walls 104, 104 may possibly adhere to the undergarment outside the rear flaps 103, 103.

In the conventional sanitary napkin 101 of FIG. 8, furthermore, the side edges 103a, 103a of the rear flaps 103, 103 are gently inclined away from the longitudinal centerline Oy-Oy. Therefore, if menstrual blood flows out of the leakage preventing walls 104, 104 near the line Lx-Lx obliquely rearward as indicated by an arrow 109, the menstrual blood tends to leak out beyond the side edges 103a, 103a of the rear flaps 103, 103. This also results in leaving a stain on the undergarment.

SUMMARY OF THE INVENTION

The present invention has been worked out in view of the shortcomings in the prior art set forth above. It is therefore an object of the present invention to provide a sanitary napkin which can effectively prevent an undergarment or the like from being stained with menstrual blood even if leakage preventing walls fall outward.

According to the present invention, there is provided a sanitary napkin comprising: an elongated main body having a skin-side surface and a garment-side surface and including a liquid absorbent layer; a pair of leakage preventing walls disposed on the skin-side surface of the main body and extending longitudinally of the main body in parallel with each other; and a pressure-sensitive adhesive layer disposed on the garment-side surface of the main body for adhering to an inner surface of an undergarment, the main body having a rear portion with rear flaps projecting from transversely opposing sides thereof, each rear flap having a starting point from which a width of the sanitary napkin starts to increase and a spreading portion in which the width gradually increases rearward from the starting point, each leakage preventing wall being composed of: a sheet that is fixed to the skin-side surface of the main body to have a longitudinally extending rising base; and an elastic member that is so tensioned between longitudinal front and rear ends of the leakage preventing wall as to raise the sheet from the skin-side surface, the rear end of the leakage preventing wall being located rearward of the starting point of the rear flap, wherein when developed transversely outward at a position between the starting point and the rear end, the sheet of the leakage preventing wall rearward of the starting point extends exclusively inside an edge of the rear flap.

In the sanitary napkin, the leakage preventing walls forward of the starting points hardly fall outward due to the presence of the thighs outside thereof. On the other hand, the leakage preventing walls rearward of the starting points tend to fall outward when a wearer lies on her back while wearing the sanitary napkin. However, even if the leakage preventing walls fall down, they never project out of the rear flaps, so that menstrual blood applied to the leakage preventing walls can be prevented from adhering to the undergarment.

In the present invention, it is preferred that when developed transversely outward at a position spaced 80±10 mm apart rearwardly from a transverse reference line on which the sanitary napkin is intended to face a center of the vaginal opening, the sheet of the leakage preventing wall extends exclusively inside the edge of the rear flap. When an average woman (Asian adult woman) wears the sanitary napkin, the leakage preventing walls do not come into contact with the thighs if they are more than 80±10 mm apart rearwardly from the center of the vaginal opening.

In the present invention, it is preferred that rearward of the spreading portion, the rear flap has an intermediate portion with a linear side edge extending longitudinally over a length equal to or greater than 60 mm. More preferably, the length is equal to or greater than 100 mm. In this sanitary napkin, since the wide intermediate portion of the rear flap extends longitudinally over at least 60 mm, preferably at least 100 mm, menstrual blood leakage can effectively be prevented over a large area. The linear side edge may be parallel with a longitudinal centerline of the sanitary napkin or so inclined as to come closer to the longitudinal centerline of the sanitary napkin rearwardly. In order to effectively prevent menstrual blood flowing obliquely rearward from reaching the undergarment, $W1/L1$ is preferably equal to or greater than 0.7, more preferably equal to or greater than 1, where $L1$ represents a length from the starting point to a front end of the linear side edge and $W1$ represents a width from the starting point to the front end of the linear side edge.

In the present invention, the skin-side surface of the main body may have an elongated main absorbent region that is surrounded by a compressed groove and intended to face the wearer's body from the vaginal opening to the cleft of the buttocks, wherein the main absorbent region has a rear end that is not spaced more than 20 mm apart longitudinally from the rear end of the leakage preventing wall.

In the present invention, it is preferred that when fully developed transversely outward, the sheet of the leakage preventing wall has a maximum width of 20 to 50 mm from the rising base.

According to the present invention, the sanitary napkin may be larger than ever such that it has a length equal to or greater than 400 mm and a width equal to or greater than 180 mm between the linear side edges of the rear flaps, relieving anxiety the undergarment may be stained with menstrual blood during sleep.

BRIEF DESCRIPTION OF THE DRAWINGS

The present invention will be understood more fully from the detailed description given hereinafter and from the accompanying drawings of the preferred embodiments of the present invention, which, however, should not be taken to limit to the invention, but are for explanation and understanding only.

In the drawings.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instances, well-known structures are not shown in detail in order not to obscure the features of the present invention.

It should be noted that the sanitary napkin, as well as its individual components, has two major surfaces: of which one surface intended to be worn toward the wearer's crotch is referred to as "skin-side surface", while the other surface is referred to as "garment-side surface". It should also be noted that unless otherwise stated, the term "length" as used herein refers to a dimension measured longitudinally of the sanitary napkin and the term "width" as used herein refers to a dimension measured transversely of the sanitary napkin.

Figure 1:
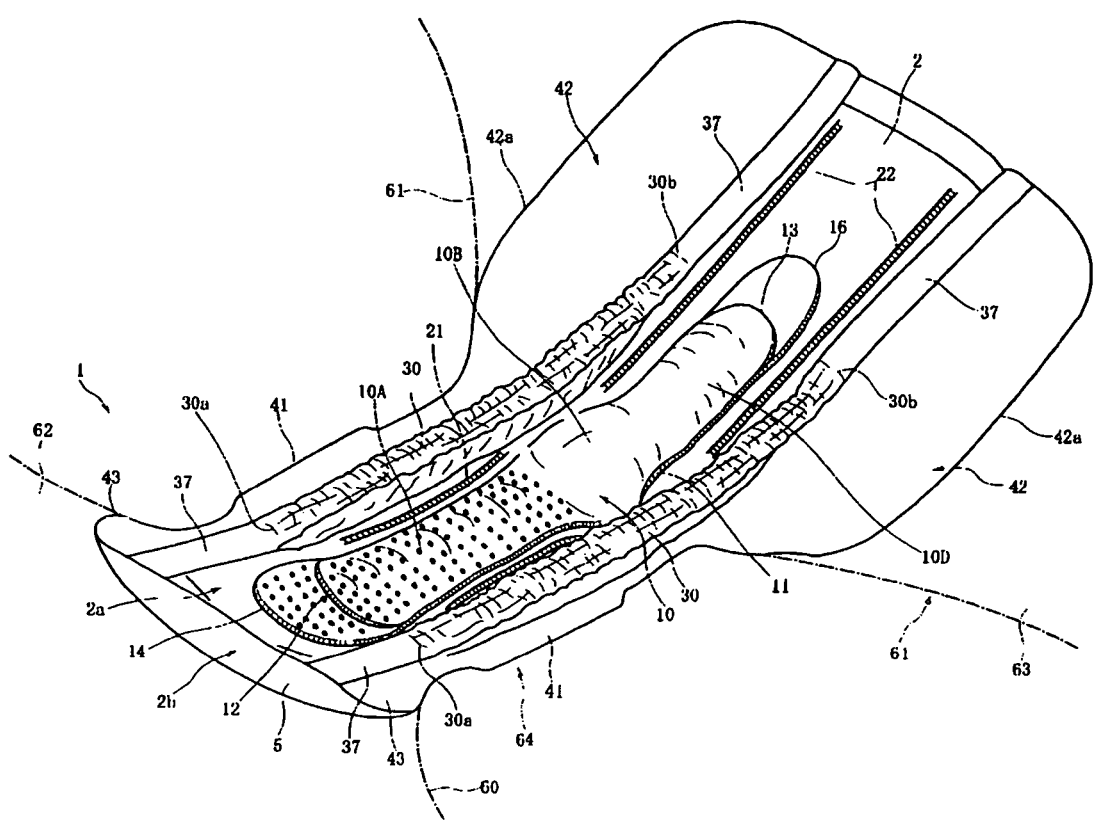
FIG. 1 is a perspective view showing a state where a sanitary napkin according to one embodiment of the present invention is placed on an undergarment.
Figure 2:
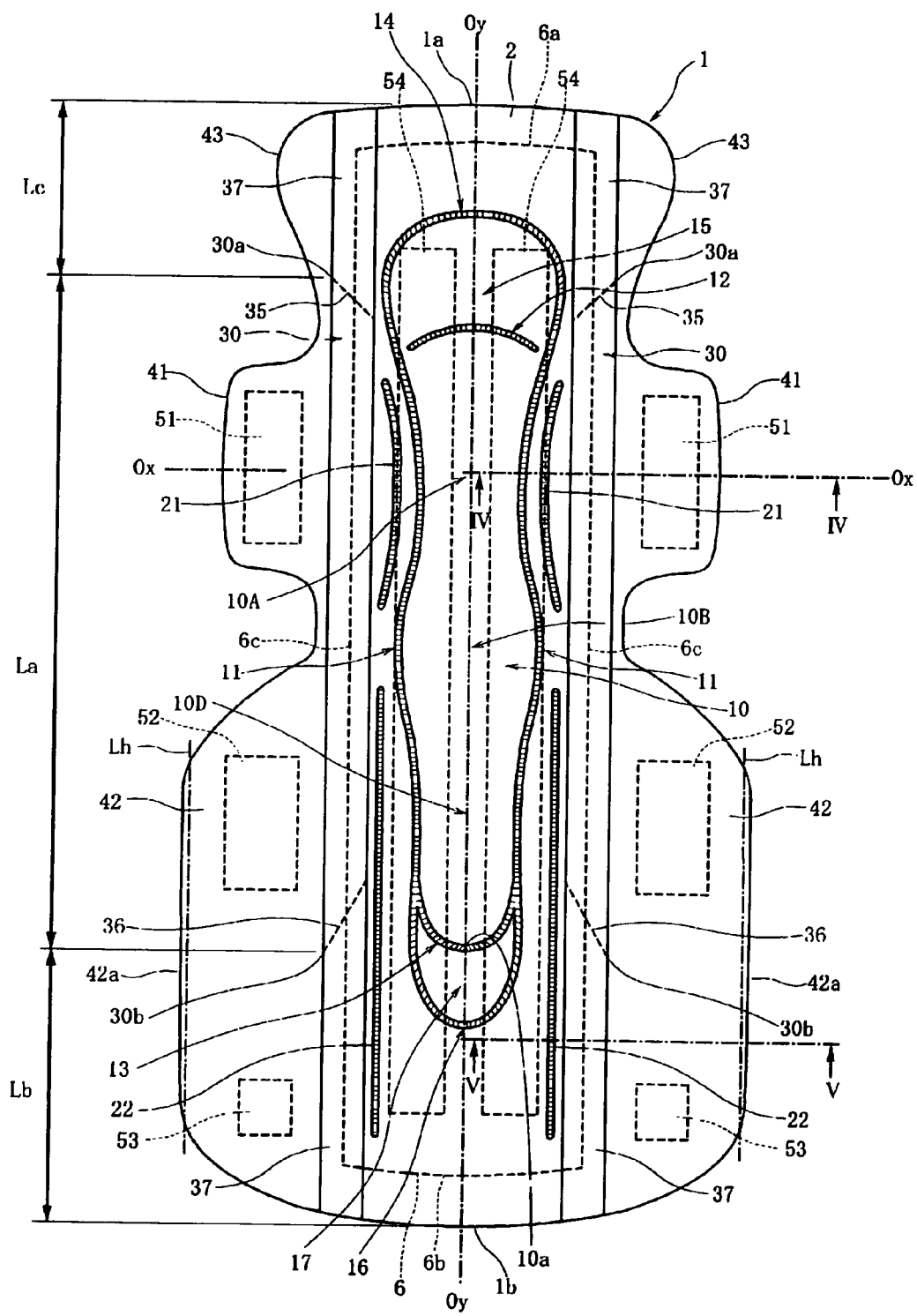
FIG. 2 is a top plan view of the sanitary napkin.
Figure 3:
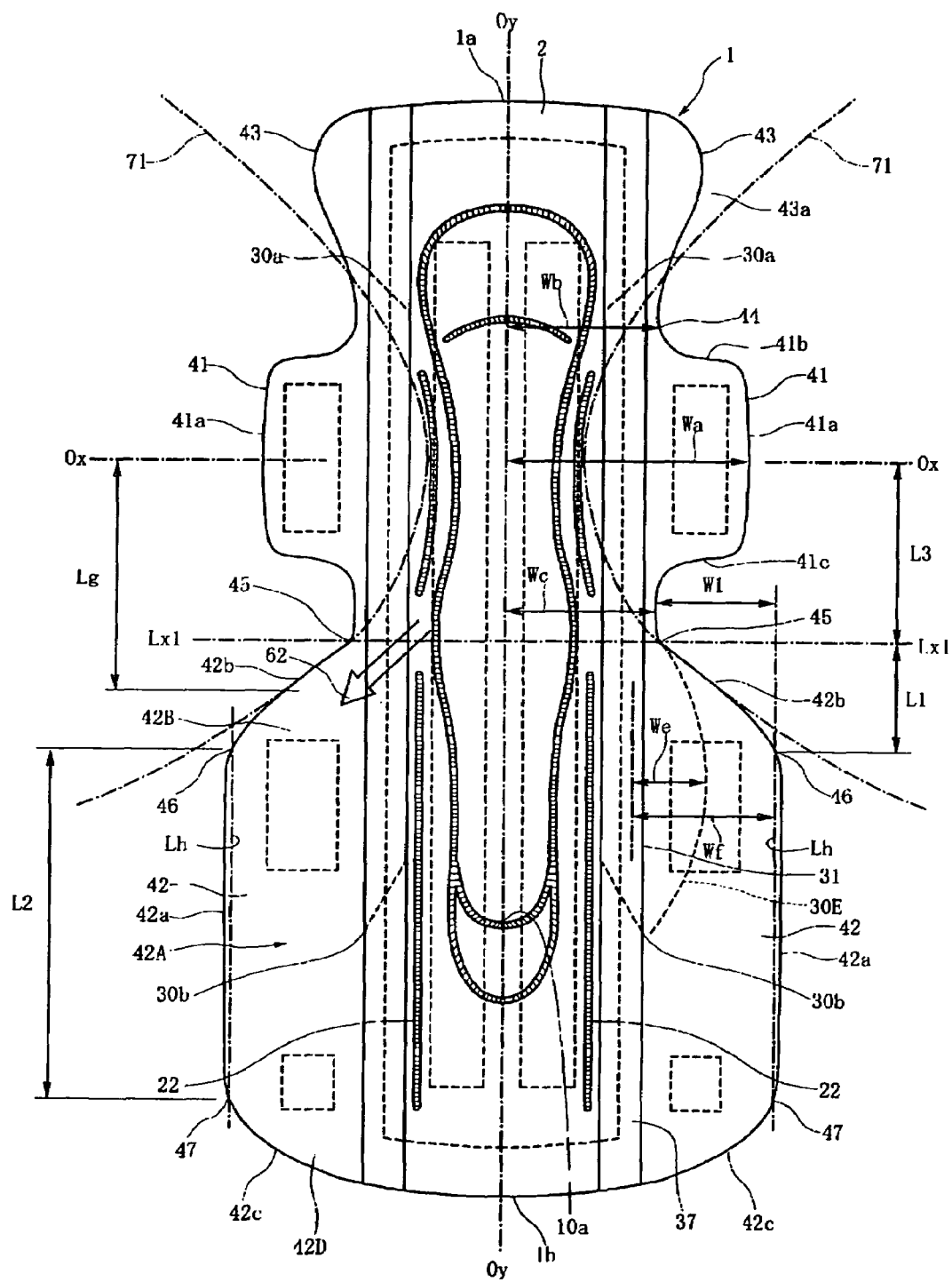
FIG. 3 is a top plan view of the sanitary napkin.
Figure 4:
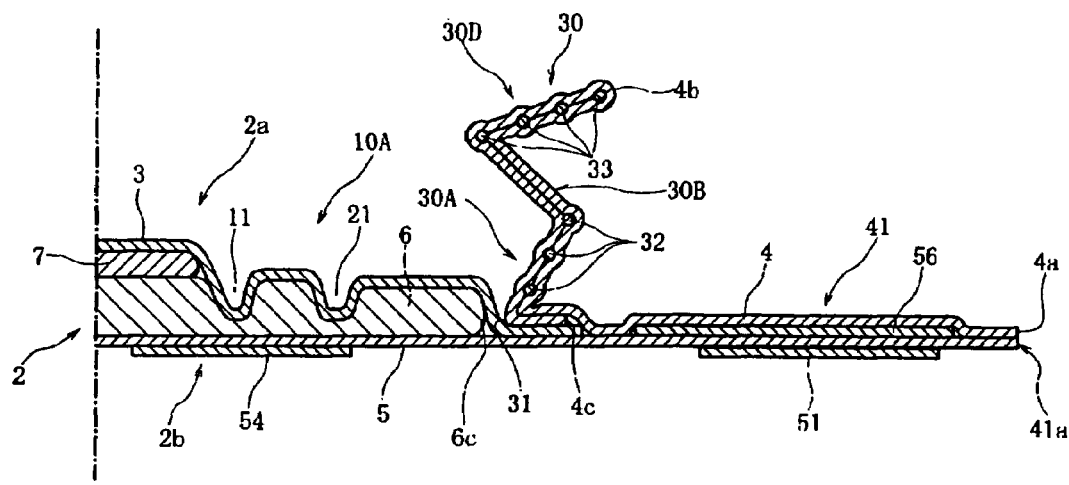
FIG. 4 is a half sectional view taken along line IV-IV of FIG. 2.
Figure 5:
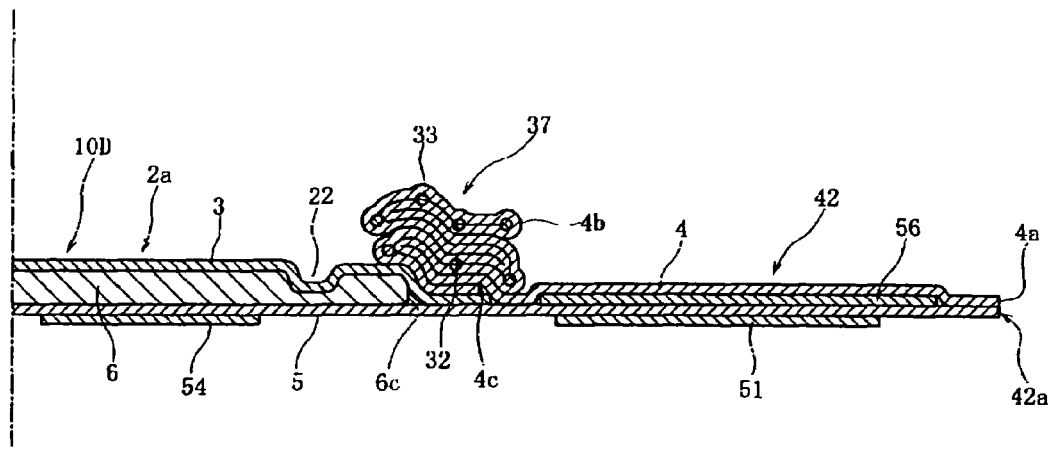
FIG. 5 is a half sectional view taken along line V-V of FIG. 2.
Figure 6:
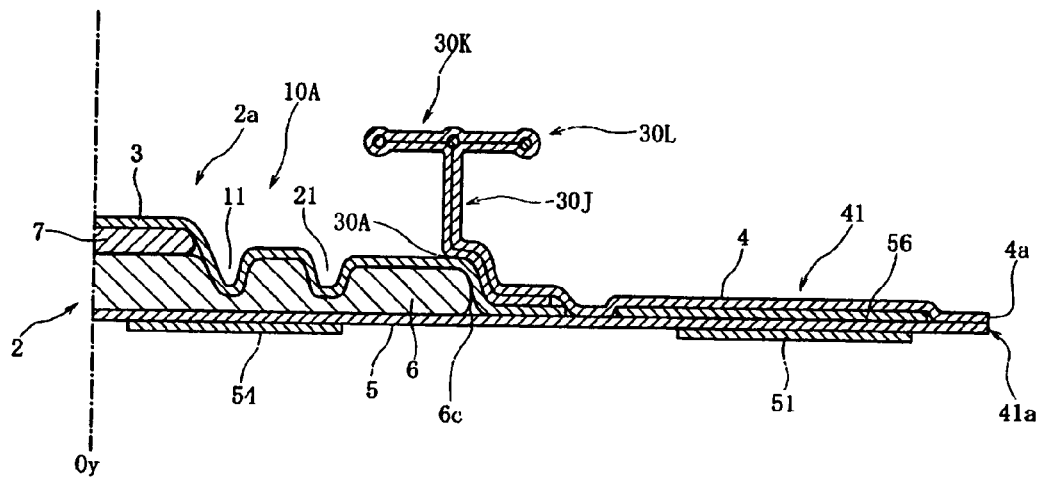
FIG. 6 is a half sectional view showing a state where a leakage preventing wall according to another embodiment is raised.
Figure 7:
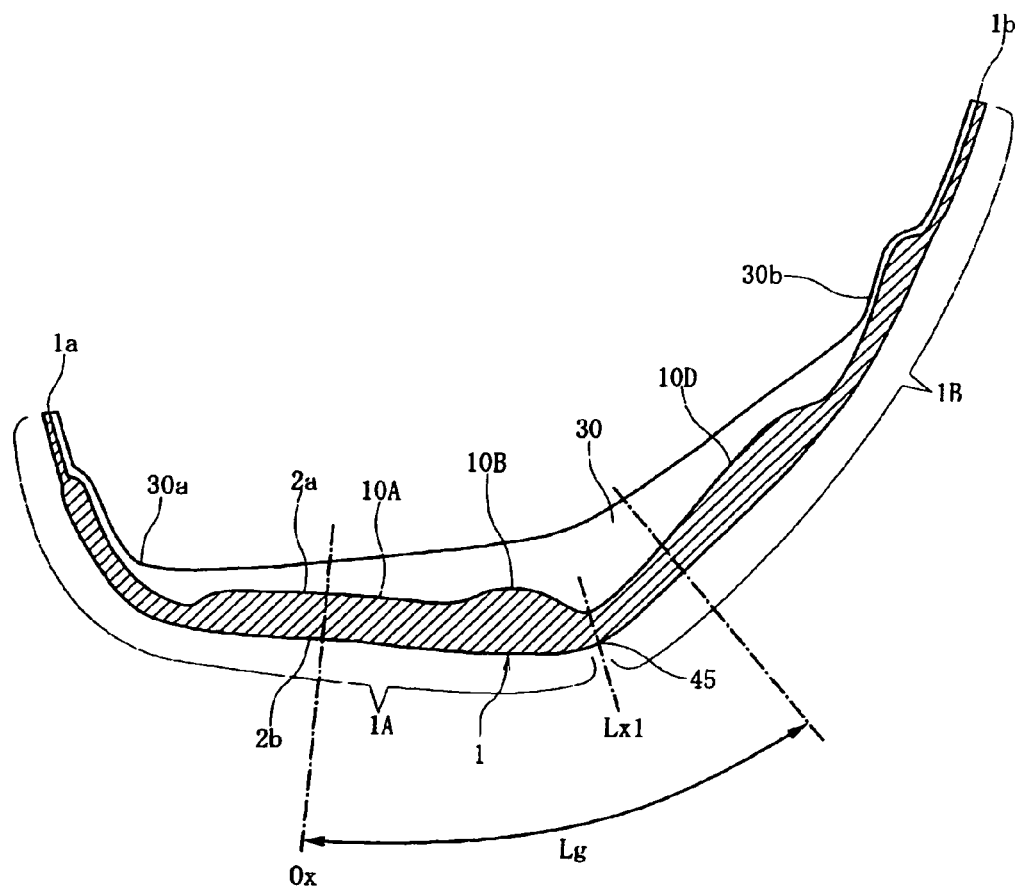
FIG. 7 is a longitudinal sectional view showing a state where the sanitary napkin is deformed.
Figure 8:
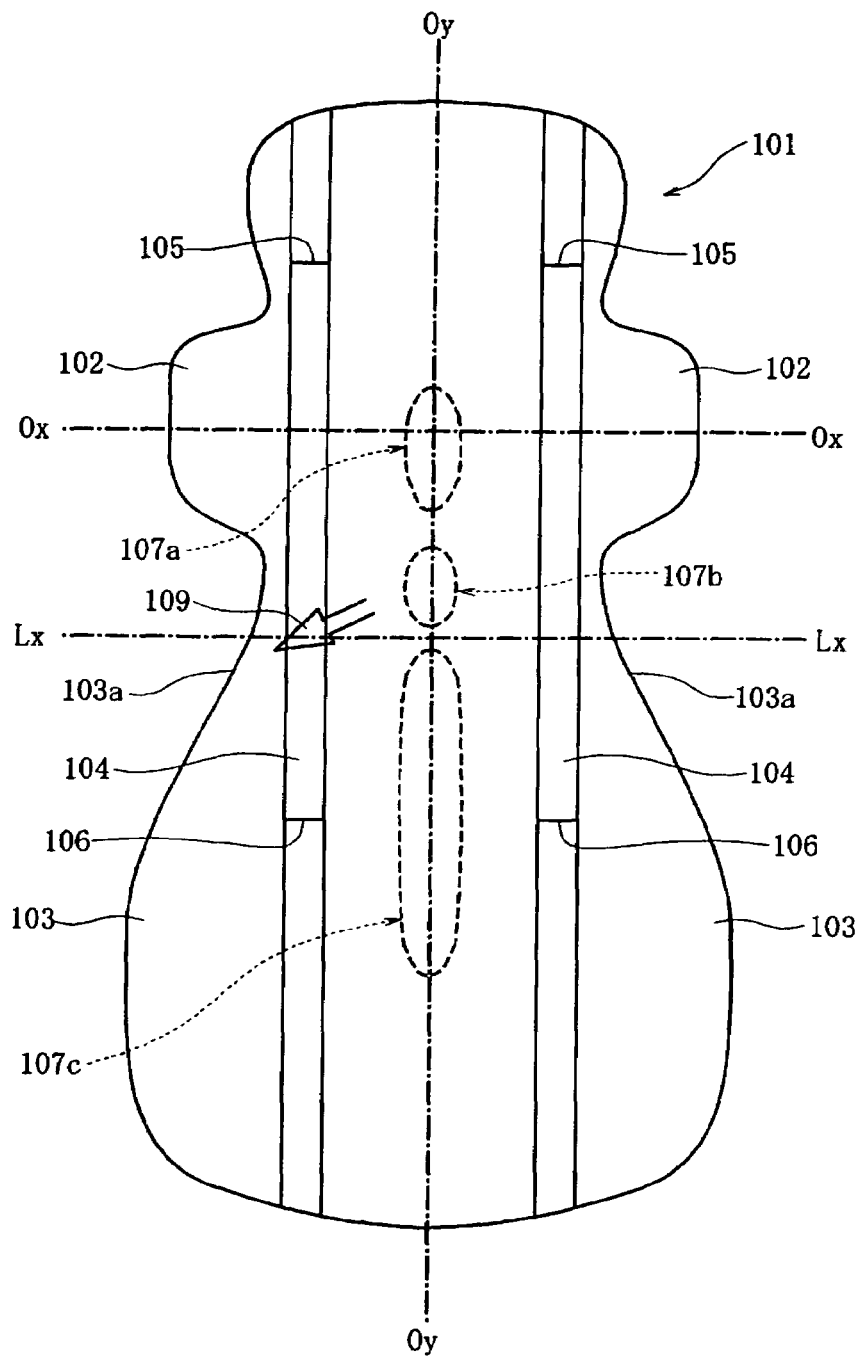
FIG. 8 is a top plan view of a conventional sanitary napkin.

FIG. 1 is a perspective view showing a state where a sanitary napkin 1 according to a first embodiment of the present invention is placed on an undergarment; FIGS. 2 and 3 are top plan views of the sanitary napkin 1; FIG. 4 is a half sectional view taken along line IV-IV of FIG. 2; FIG. 5 is a half sectional view taken along line V-V of FIG. 2; FIG. 6 is a half sectional view showing a state where a leakage preventing wall according to another embodiment is raised; and FIG. 7 is a longitudinal sectional view showing a state where the sanitary napkin 1 is deformed during wear.

According to the first embodiment shown in FIGS. 1-5, the sanitary napkin 1 comprises: an elongated main body 2 having a skin-side surface 2a and a garment-side surface 2b; and a pair of leakage preventing walls 30, 30 that are allowed to rise from the skin-side surface 2a of the main body 2.

In FIG. 2, the sanitary napkin 1, which is slightly curved in FIG. 1, is shown in a fully opened (or flattened) state. FIG. 2 shows a longitudinal centerline Oy-Oy coinciding with midpoints of front and rear end edges 1a, 1b of the sanitary napkin 1, wherein the sanitary napkin 1 has bilateral symmetry about the longitudinal centerline Oy-Oy. FIG. 2 also shows a transverse reference line Ox-Ox on which the sanitary napkin 1 is intended to face the center of the vaginal opening during wear. In the present embodiment with fold-back flaps 41, 41, the transverse reference line Ox-Ox substantially coincides with a line which longitudinally bisects the fold-back flaps.

As shown in FIGS. 4 and 5, a liquid-permeable topsheet 3 appears on the skin-side surface 2a of the main body 2 in a region between the leakage preventing walls 30, 30; a side sheet 4 appears outside each leakage preventing wall 30. In the present embodiment, the side sheet 4 forms the leakage preventing wall 30. On the other hand, a liquid-impermeable backsheet 5 appears on the garment-side surface 2b of the main body 2.

The main body 2 has a liquid absorbent layer 6 disposed between the topsheet 3 and the backsheet 5. As shown in FIG. 2, the liquid absorbent layer 6 is of an almost rectangular shape. The liquid absorbent layer 6 has a front end edge 6a slightly inside the front end edge 1a of the sanitary napkin 1 and a rear end edge 6b slightly inside the rear end edge 1b of the sanitary napkin 1. The liquid absorbent layer 6 has transversely opposite side edges 6c inside rising bases 31 of the leakage preventing walls 30. However, the side edges 6c may be located outside the rising bases 31.

In the skin-side surface 2a, compressed grooves where the topsheet 3 and the liquid absorbent layer 6 are compressed are formed in the region between the leakage preventing walls 30, 30. The compressed grooves comprise: longitudinal compressed grooves 11, 11 extending longitudinally in a curved manner; a front transverse compressed groove 12 located between front portions of the longitudinal compressed grooves 11, 11; and a rear transverse compressed groove 13 connecting rear portions of the longitudinal compressed grooves 11, 11.

The region surrounded by the longitudinal compressed grooves 11, 11, the front transverse compressed groove 12, and the rear transverse compressed groove 13 is referred to as elongated main absorbent region 10. The main absorbent region 10 includes a front main absorbent region 10A, an intermediate main absorbent region 10B, and a rear main absorbent region 10D.

In the front main absorbent region 10A, the right and left longitudinal compressed grooves 11, 11 are curved toward the longitudinal centerline Oy-Oy, wherein the distance between the longitudinal compressed grooves 11, 11 is smallest near the transverse reference line Ox-Ox. In the intermediate main absorbent region 10B, the longitudinal compressed grooves 11, 11 are curved away from the longitudinal centerline Oy-Oy. The rear main absorbent region 10D is elongated longitudinally of the napkin, in which the distance between the longitudinal compressed grooves 11, 11 is smaller than in the intermediate main absorbent region 10B.

In the center absorbent region 10, a bulky, liquid permeable layer (cushion layer) 7 of a lower density than the liquid absorbent layer 6 is disposed between the topsheet 3 and the liquid absorbent layer 6, as shown in FIG. 4.

Forward of the front transverse compressed groove 12 is provided a front outside compressed groove 14, as shown in FIG. 2. The front outside compressed groove 14 is curved forward and connects the right and left longitudinal compressed grooves 11, 11. The region surrounded by the front transverse compressed groove 12 and the front outside compressed groove 14 is referred to as front auxiliary absorbent region 15. Rearward of the rear transverse compressed groove 13 is provided a rear outside compressed groove 16. The longitudinal compressed grooves 11, 11, the rear transverse compressed groove 13, and the rear outside compressed groove 16 are connected together, and both the rear transverse compressed groove 13 and the rear outside compressed groove 16 are curved rearward. Here, the region surrounded by the rear transverse compressed groove 13 and the rear outside compressed groove 16 is referred to as rear auxiliary absorbent region 17.

In the sanitary napkin 1, the elongated region surrounded by the longitudinal compressed grooves 11, 11, the front outside compressed groove 14, and the rear outside compressed groove 16 is raised higher than the remaining region outside it. Of the raised portion, the main absorbent region 10 is raised much higher.

On both right and left sides of the front main absorbent region 10A, first outside longitudinal compressed grooves 21, 21 are provided outside and at a distance apart from the longitudinal compressed grooves 11, 11. The first outside longitudinal compressed grooves 21, 21 are also curved toward the longitudinal centerline Oy-Oy, wherein the distance therebetween is smallest near the transverse reference line Ox-Ox.

On both right and left sides of the rear main absorbent region 10D, second outside longitudinal compressed grooves 22, 22 are provided at a distance transversely apart from the longitudinal compressed grooves 11, 11. The second outside longitudinal compressed grooves 22, 22 extend longitudinally in substantially parallel relation to the longitudinal centerline Oy-Oy. It should be noted that they extend rearward from a boundary between the intermediate main absorbent region 10B and the rear main absorbent region 10D to have their rear ends farther rearward than the rear outside compressed groove 16.

The individual compressed grooves are formed by heating the topsheet 3 and the liquid absorbent layer 6 under pressure from the side of the topsheet 3. At the bottoms of the individual compressed grooves, high-density compressed portions (highly compressed portions) and medium-density compressed portions (portions whose density is slightly lower than the high-density compressed portions) alternate with each other along the linear pattern of the compressed grooves so that the grooves are of a sufficient depth overall.

As shown in FIGS. 4 and 5, the side sheet 4 has an edge 4a coinciding with the outer edge of the backsheet 5. The side sheet 4 has a single-layer portion and a multi-layer portion, wherein the single-layer portion is bonded to the backsheet 5 or other materials disposed on the backsheet 5, whereas the multi-layer portion forms the leakage preventing wall 30 (see FIG. 4) or a stacked/fixed portion 37 (see FIG. 5). In the multi-layer portion, at first, the side sheet 4 is folded on its fold line 4b to have an edge 4c on the topsheet 3. In FIG. 4, the side sheet 4 is bonded to the topsheet 3 from the rising base 31 to the edge 4c.

Confronting surfaces of the side sheet 4 thus folded in two are bonded together through a hot-melt type adhesive with a plurality of elastic members 32, 33 disposed therebetween. The individual elastic members 32, 33 extend longitudinally over the entire length of the leakage preventing wall 30 and beyond the front and rear ends 30a, 30b. The elastic members 32, 33 are bonded to the side sheet 4 while being longitudinally stretched to a predetermined degree.

In an area of a length Lb from a rear bond edge 36 to the rear end edge 1b (see FIG. 2), the multi-layer portion of the side sheet 4 previously folded in two is further folded in three, as shown in FIG. 5, wherein these layers are bonded to each other as well as to the topsheet 3, thereby forming the stacked/fixed portion 37. Also in an area of a length Lc from a front bond edge 35 to the front end edge 1a, the multi-layer portion of the side sheet 4 is similarly folded and bonded, forming the stacked/fixed portion 37.

The front bond edge 35 and the rear bond edge 36 extend obliquely with respect to both the longitudinal direction and the transverse direction. Between the front bond edge 35 and the rear bond edge 36, the multi-layer portion of the side sheet 4 previously folded in two forms the leakage preventing wall 30 that can rise from the skin-side surface 2a, as shown in FIG. 4. It should be noted that the front end 30a of the leakage preventing wall 30 refers to one end of the front bond edge 35 that is closer to the front end edge 1*a*, and the rear end 30*b* of the leakage preventing wall 30 refers to one end of the rear bond edge 36 that is closer to the rear end edge 1*b*. The length of the leakage preventing wall 30 refers to a dimension measured La from the front end 30*a* to the rear end 30*b*.

The elastic members 32, 33 exert an elastic contractive force between the front end 30*a* and the rear end 30*b*, so that an elastic force acts to bring the front end 30*a* and the rear end 30*b* closer to each other, whereby the main body 2 is curved as shown in FIG. 1 and each side sheet 4 is raised from the skin-side surface 2*a* between the front end 30*a* and the rear end 30*b*, providing the leakage preventing wall 30.

Because the side sheet 4 at the stacked/fixed portion 37 is folded in a multi-layer structure and then bonded and fixed as shown in FIG. 5, the leakage preventing wall 30 includes: a lower inclined panel 30A extending obliquely upward from the rising base 31 toward the outside; an intermediate inclined panel 30B extending obliquely upward from the upper end of the lower inclined panel 30A toward the longitudinal centerline Oy-Oy; and a skin-contacting panel 30D extending obliquely upward from the upper end of the intermediate inclined panel 30B toward the outside, as shown in the half sectional view of FIG. 4.

Referring to FIG. 3, the main body 2 of the sanitary napkin 1 will be described hereinbelow with respect to the shape. It should be noted that FIG. 3 is a top plan view showing the same sanitary napkin 1 as the top plan view of FIG. 2.

Along the transverse reference line Ox-Ox, the fold-back flaps 41 are disposed to project transversely outward from the main body 2. Each fold-back flap 41 extends over a given length with center at the transverse reference line Ox-Ox. Rearward of the fold-back flaps 41 are disposed rear flaps 42 also projecting transversely outward from the main body 2; forward of the fold-back flaps 41 are disposed front flaps 43 projecting transversely outward from the main body 2. Since the sanitary napkin 1 has bilateral symmetry about the longitudinal centerline Oy-Oy, the right and left flaps are of symmetrical shape.

As used herein, the term "half-width" refers to a dimension measured transversely from the longitudinal centerline Oy-Oy to one side edge of the sanitary napkin 1.

The half-width from the longitudinal centerline Oy-Oy to a side edge 41*a* of the fold-back flap 41 is largest on the transverse reference line Ox-Ox, wherein Wa designates the largest half-width. The side edge 41*a* is generally parallel to the longitudinal centerline Oy-Oy so as to provide an almost constant half-width over a given length of the side edge 41*a*. Between the fold-back flap 41 and the front flap 43 is provided a first narrowest portion of a smallest half-width Wb. At the first narrowest portion, the napkin's edge provides a first starting point 44. The fold-back flap 41 has a front edge 41*b* that is curved to gradually increase the half-width rearward from the first starting point 44 and continue to the side edge 41*a*.

The front flap 43 has a side edge 43*a* that is curved to gradually increase the half-width forward from the first starting point 44.

Between the fold-back flap 41 and the rear flap 42 is provided a second narrowest portion of a smallest half-width Wc. The fold-back flap 41 has a rear edge 41*c* that is curved to gradually increase the half-width forward from the second narrowest portion and continue to the side edge 41*a*.

At the second narrowest portion, the napkin's edge provides a second starting point 45 from which the half-width starts to increase rearward. The rear flap 42 extends from the second starting point 45 to the rear end edge 1*b* of the sanitary napkin 1.

The rear flap 42 may be divided in three areas: an intermediate portion 42A; a front spreading portion 42B; and a rear converging portion 42D.

In the intermediate portion 42A, the rear flap 42 has a linear side edge 42*a* extending over a length L2. As used herein, the term "linear side edge" should not be construed as limited to an edge extending in a perfect straight line, but may extend with a deviation within a range of ±5 mm transversely from an imaginary straight line Lh that intersects with the edge of the rear flap at two points (the two intersections are spaced by L2). In the present embodiment, the side edge 42*a* of the intermediate portion 42A is slightly curved outward as shown in FIGS. 2 and 3. Therefore, the imaginary straight line Lh is set so as not to be spaced more than 5 mm inwardly apart from the side edge 42*a*, wherein front and rear intersections between the imaginary straight line Lh and the edge of the rear flap are referred to as front and rear boundary points 46, 47, respectively.

If the side edge 42*a* is a perfect straight line, front and rear ends of the linear side edge 42*a* may be the front and rear boundary points 46, 47, respectively.

The side edge 42*a* or the imaginary straight line Lh may be parallel to the longitudinal centerline Oy-Oy. In an alternative, the side edge 42*a* or the imaginary straight line Lh may be so inclined as to come closer to the longitudinal centerline Oy-Oy rearwardly.

The front spreading portion 42B extends from the second starting point 45 to the front boundary point 46. The front spreading portion 42B has an edge 42*b* that is curved to gradually increase the half-width rearward from the second starting point 45 to the front boundary point 46. Here, W1/L1 is preferably equal to or greater than 0.7, more preferably equal to or greater than 1, where W1 represents a width from the second starting point 45 to the front boundary point 46 and L1 represents a length from the second starting point 45 to the front boundary point 46. The upper limit of W1/L1 is preferably about 2. With this construction, the edge 42*b* may be curved so that the front spreading portion 42B sharply spreads transversely.

Rearward of the rear boundary point 47, the rear flap 42 has the rear converging portion 42D. The rear converging portion 42D has an edge 42*c* that is curved to gradually decrease the half-width rearward from the rear boundary point 47 to the rear end edge 1*b*.

In the present embodiment in which the side edge 42*a* extends linearly over the length L2, the rear flap 42 has an appropriate width although extending over a large area.

Hereinbelow, preferred dimensions of the individual portions, as well as dimensional relationships between the portions, will be described. Dimensions of the main body 2 are measured with the sanitary napkin 1 being developed flat as shown in FIGS. 2 and 3.

The half-width Wb at the first starting point 44 located forward of the fold-back flap 41 is almost equal to the half-width Wc at the second starting point 45 located forward of the rear flap 42. The half-width from the longitudinal centerline Oy-Oy to side edge 42*a* of the rear flap 42 is larger than that to the side edge 41*a* of the fold-back flap 41.

The main absorbent region 10 between the longitudinal compressed grooves 11, 11 has a width of 10 to 40 mm, and the side edges 6*c*, 6*c* of the liquid absorbent layer 6 are located outside the longitudinal compressed grooves 11, 11 and the first outside longitudinal compressed grooves 21, 21.

A length L3 from the transverse reference line Ox-Ox to the second starting point 45 is in the range of 40 to 70 mm. With the length L3 being set within the range and W1/L1 being equal to or greater than 0.7, the edge 42*b* of the front spreading portion 42B may extend along the edge of the leg opening of the undergarment without projecting into the leg opening.

The length L2 of the linear side edge 42a of the intermediate portion 42A of the rear flap 42, i.e., the length from the front boundary point 46 to the rear boundary point 47 is at least ⅓ of the length from the second starting point 45 to the rear end edge 1b. The length L2 is preferably equal to or greater than 60 mm, more preferably equal to or greater than 100 mm. The upper limit of L2 is preferably (but not limited to) about 200 mm. The rear flaps 42, 42 extend over a large area longitudinally and transversely, improving the effect of preventing transverse leakage of menstrual blood.

The length of the rear flap 42, i.e., the length from the second starting point 45 to the rear end edge 1b is preferably equal to or greater than 40%, more preferably equal to or greater than 50% the length from the front end edge 1a to the rear end edge 1b. The sanitary napkin 1 may be larger than the conventional one in both length and width. The length is equal to or greater than 400 mm, preferably equal to or greater than 410 mm and its upper limit is (but not limited to) about 500 mm. On the other hand, the width (i.e., a maximum distance between the side edges 42a, 42a of the rear flaps 42, 42) is equal to or greater than 180 mm and its upper limit is (but not limited to) about 300 mm.

The main absorbent region 10 has a length capable of covering a region from the vaginal opening to the cleft of the buttocks and may be equal to or greater than 120 mm.

The rear end 30b of the leakage preventing wall 30 is located farther rearward than the second starting point 45 and the front boundary point 46, wherein the length from the second starting point 45 to the rear end 30b is equal to or greater than 30 mm, preferably equal to or greater than 50 mm. On the other hand, the rear end 30b of the leakage preventing wall 30 is not spaced more than 20 mm apart longitudinally from the rear end 10a of the main absorbent region 10. The length of the leakage preventing wall 30 from the front end 30a to the rear end 30b is equal to or greater than 120 mm.

When the side sheet 4 forming the leakage preventing wall 30 is fully developed transversely outward between the front end 30a and the rear end 30b, the side sheet 4 preferably has a maximum width of 20 to 50 mm from the rising base 31 of the leakage preventing wall 30.

When thus fully developed between the front end 30a and the rear end 30b, the leakage preventing wall 30 projects transversely outward beyond the first and second starting points 44, 45. At a distance Lg or more rearwardly from the transverse reference line Ox-Ox, however, the edge 42b of the front spreading portion 42B does not coincide with the edge of the fully developed leakage preventing wall 30.

When the sanitary napkin 1 is worn, the leakage preventing wall 30 near the transverse reference line Ox-Ox is supposed to come into contact with the thigh. At the distance Lg or more rearwardly from the transverse reference line Ox-Ox, on the other hand, the leakage preventing wall 30 does not come into contact with the thigh. In case of an average Asian adult woman, the distance Lg is 80±10 mm.

Even when the leakage preventing wall 30 not in contact with the thigh falls outward during wear, however, the edge 42b of the front spreading portion 42B is present outside the fallen leakage preventing wall 30, so that the undergarment can be prevented from being stained with body liquid on the fallen leakage preventing wall 30.

In FIG. 3, a free end 30E of the leakage preventing wall 30 that is developed transversely outward between the second starting point 45 and the rear end 30b is shown with a dotted line, wherein the leakage preventing wall 30 is constrained at the second starting point 45 so as not to project transversely beyond the starting point 45. As shown in FIG. 3, the front spreading portion 42B of the rear flap 42 sharply spreads transversely, W1/L1 is equal to or greater than 0.7, and the half-width from the longitudinal centerline Oy-Oy to the imaginary straight line Lh is significantly large. Accordingly, the free end 30E of the leakage preventing wall 30 does not project transversely beyond the edge 42b of the front spreading portion 42B or the linear side edge 42a of the intermediate portion 42A.

Between the second starting point 45 and the rear end 30b, as mentioned above, the fallen leakage preventing wall 30 has a maximum width We of 20 to 50 mm from the rising base 31. On the other hand, a width Wf from the rising base 31 to imaginary straight line Lh is at least 5 mm, preferably at least 10 mm larger than the width We. The width Wf is in the range of 25 to 60 mm.

On the garment-side surface of the sanitary napkin 1, there are disposed pressure-sensitive adhesive layers, as shown in FIG. 2. The fold-back flap 41 has a front pressure-sensitive adhesive layer 51. The rear flap 42 has first and second rear pressure-sensitive adhesive layers 52, 53 that are separate from each other in the longitudinal direction. Furthermore, central pressure-sensitive adhesive layers 54 are disposed on each side of the longitudinal centerline Oy-Oy. The central pressure-sensitive adhesive layers 54 are located inside the rising bases 31 of the leakage preventing walls 30 and extend longitudinally within the region of the liquid absorbent layer 6.

In the fold-back flap 41, as shown in FIGS. 4 and 5, a reinforcing sheet 56 is interposed between and bonded to the backsheet 5 and the side sheet 4. Also in the rear flap 42, a reinforcing sheet 57 is interposed between and bonded to the backsheet 5 and the side sheet 4.

Next, preferred examples of the individual components of the sanitary napkin 1 will be described.

The topsheet 3 is a liquid-permeable sheet, such as a through-air bonded nonwoven fabric, a spunlaced nonwoven fabric, or an apertured resin film (resin film formed with a large number of liquid passage holes). The backsheet 5 is a resin film that is impermeable to liquid but may be breathable.

The liquid absorbent layer 6 may be a layer of pulp, a layer of pulp and superabsorbent polymer, or an air-laid nonwoven fabric in which only pulp or pulp and rayon are deposited by air-laid process and the fibers are fixed together through an adhesive. The liquid permeable layer 7 is a bulky nonwoven fabric of a three-dimensional network structure, such as a through-air bonded nonwoven fabric or an air-laid nonwoven fabric in which pulp and synthetic fibers are deposited by air-laid process and the fibers are fixed together through an adhesive.

The side sheet 4 is impermeable to liquid and is preferably treated to be water-repellent. The side sheet 4 may be a meltblown nonwoven fabric, a spunbonded nonwoven fabric, or a laminated composite of spunbond/meltblown/spunbond.

The reinforcing sheets 56, 57 may be of a spunbonded nonwoven fabric, a point-bonded nonwoven fabric, a meltblown nonwoven fabric, or a paper material. The pressure-sensitive adhesive layers 51, 52, 53 and 54 may be of a rubber-based hot-melt type adhesive.

Hereinbelow, the function of the sanitary napkin 1 will be described.

FIG. 1 shows a state where the sanitary napkin 1 is attached to an undergarment 60 such as a sanitary panty. The undergarment 60 has leg openings 61, 61. Between a front body 62 and a rear body 63, the undergarment 60 has a crotch part 64 on which the front portion of the sanitary napkin 1 is placed.

Through the central pressure-sensitive adhesive layers 54, the garment-side surface 2b of the main body 2 is adhered to the inner surface of the undergarment 60 from the crotch part 64 to the lower part of the back body 63. The fold-back flaps 41 are folded back along the side edges of the crotch part 64 of the undergarment 60 and the front pressure-sensitive adhesive layers 51 on the fold-back flaps 41 are adhered to the outer surface of the crotch part 64. The rear flaps 42 kept in a developed state are adhered to the inner surface of the lower part of the back body 63 through the first rear pressure-sensitive adhesive layers 52 and the second rear pressure-sensitive adhesive layers 53.

When the undergarment 60 is worn, the longitudinal central portion of the front main absorbent region 10A, i.e., the intersection of the longitudinal centerline Oy-Oy and the transverse reference line Ox-Ox and its surrounding area may come into contact with the woman's vaginal opening, the intermediate portion between the front main absorbent region 10A and the intermediate main absorbent region 10B may confront the perineum, and the intermediate main absorbent region 10B may confront the anus. Accordingly, the rear main absorbent region 10D may extend along the cleft of the buttocks and the rear auxiliary absorbent region 17 may confront the coccyx.

In the sanitary napkin 1, the skin-side surface 2a tends to be recessed as shown in FIG. 1 due to the longitudinal elastic contractive force of the leakage preventing walls 30, whereby the leakage preventing walls 30 are raised from the skin-side surface 2a.

FIG. 3 shows pressure surfaces 71, 71 on both sides of the sanitary napkin 1. The pressure surfaces 71, 71 represent surfaces from which a compressive force (clamping force) is exerted on the sanitary napkin 1 when the sanitary napkin 1 is held between the wearer's thighs.

When the sanitary napkin 1 is subjected to a compressive force from the pressure surfaces 71, 71, the compressive force may concentrate in the front main absorbent region 10A and the intermediate main absorbent region 10B. Particularly in the front main absorbent region 10A, the liquid absorbent layer 6 is transversely compressed. With such compression, the front main absorbent region 10A held between the longitudinal compressed grooves 11, 11 is raised toward the wearer's body, facilitating close contact with the vaginal opening and its surrounding region. In addition, since the undergarment exerts a tightening force on the intermediate main absorbent region 10B and the rear main absorbent region 10D along the longitudinal centerline Oy-Oy, the intermediate main absorbent region 10B and the rear main absorbent region 10D can fit in the cleft of the buttocks when the wearer is in a standing position, minimizing the space between the sanitary napkin 1 and the wearer's body.

In FIG. 7, front and rear portions of the sanitary napkin 1 are indicated by 1A and 1B, respectively, and the boundary therebetween is indicated by a line Lx1-Lx1. When the wearer of the sanitary napkin 1 lies on her back during sleep, the buttocks exert a pressure on the sanitary napkin 1 so that the rear portion 1B is compressed flat. Near the line Lx1-Lx1, accordingly, the rear portion 1B tends to be bent from the front portion 1A, leaving a space between the skin-side surface 2a of the main body 2 and the wearer's body.

In the sanitary napkin 1, however, since the rear flaps 42 project transversely outward from the second starting points 45 coinciding with the line Lx1-Lx1 so that the edges 42b of the front spreading portions 42B extend along the edges of the leg openings 61 of the undergarment 60, menstrual blood flowing obliquely rearward beyond the leakage preventing wall 30 as indicated by an arrow 62 can be effectively prevented from leaking out.

Here, the leakage preventing walls 30, 30 in contact with the thighs hardly fall outward, and therefore, can easily be kept in a position rising from the skin-side surface 2a. However, the leakage preventing walls 30, 30 do not come into contact with the thighs at the distance Lg or more, easily causing outward fall of the leakage preventing walls 30, 30. Particularly when the wearer lies on her back during sleep, the leakage preventing walls 30, 30 tend to fall flat due to the pressure exerted on the rear portion 1B from the buttocks.

However, even when the leakage preventing wall 30 is fully developed transversely outward, the leakage preventing wall 30 does not project beyond the edge 42b of the front spreading portion 42B at the distance Lg or more. Furthermore, even when the leakage preventing wall 30 is developed transversely outward at a position between the second starting point 45 and the rear end 30b, the free end 30E does not project beyond the edge of the rear flap 42. Accordingly, menstrual blood on the leakage preventing wall 30 hardly comes into contact with the undergarment 60.

The leakage preventing wall may be of any rising position. For instance, FIG. 6 shows a leakage preventing wall 30L with a rising base 31A over the liquid absorbent layer 6. At an upper end of a rising wall panel 30J, a skin-contacting panel 30K projects both toward and away from the longitudinal centerline Oy-Oy.

According to the present invention, as has been described hereinabove, an undergarment can be effectively prevented from being stained with menstrual blood flowing obliquely rearward during sleep.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the features set out in the appended claims.

What is claimed is:

1. A sanitary napkin comprising:
   an elongated main body having a skin-side surface and a garment-side surface and including
   a liquid absorbent layer;
   a pair of leakage preventing walls disposed on the skin-side surface of the main body and extending longitudinally of the main body in parallel with each other; and
   a pressure-sensitive adhesive layer disposed on the garment-side surface of the main body for adhering to an inner surface of an undergarment,
   the main body having a front portion with front flaps projecting from transversely opposing sides thereof, each front flap having a first starting point disposed on each of opposing side edge portions of the sanitary napkin from which a width of the sanitary napkin starts to increase and a first spreading portion in which the width gradually increases forward from the first starting point,
   the main body further having a rear portion with rear flaps projecting from transversely opposing sides thereof, each rear flap having a second starting point disposed on each of the opposing side edge portions of the sanitary napkin from which a width of the sanitary napkin starts to increase and a second spreading portion in which the width gradually increases rearward from the second starting point, each of the pair of leakage preventing walls having
a sheet that is folded and fixed to the skin-side surface of the main body to have a longitudinally extending rising base, and
an elastic member that is so tensioned between longitudinal front and rear ends of the leakage preventing wall as to raise the sheet from the skin-side surface, the rear end of the leakage preventing wall being located rearward of the second starting point of the rear flap, wherein, when one of the leakage preventing walls is fully stretched transversely outward from between its longitudinal front and rear ends, the stretched sheet of the leakage preventing wall projects transversely outward beyond one of the first starting points of the front flaps and one of the second starting points of the rear flaps, and when the one leakage preventing wall is stretched transversely outward within an area between the one second starting point and the rear end of the one leakage preventing wall, while being restrained from being stretched transversely outward within an area between the one second starting point and the front end of the one leakage preventing wall, the stretched sheet of the leakage preventing wall is prevented from projecting beyond an edge of the second spreading portion of the rear flap.

2. A sanitary napkin according to claim 1, wherein, when fully stretched transversely outward, the sheet of the leakage preventing wall is prevented from projecting beyond the edge of the second spreading portion of the rear flap at a position spaced 80±10 mm apart rearwardly from a transverse reference line on which the sanitary napkin is intended to face a center of the vaginal opening.

3. A sanitary napkin according to claim 1, wherein rearward of the second spreading portion, the rear flap has an intermediate portion with a linear side edge extending longitudinally over a length equal to or greater than 60 mm.

4. A sanitary napkin according to claim 3, wherein the linear side edge is parallel with a longitudinal centerline of the sanitary napkin.

5. A sanitary napkin according to claim 3, wherein the linear side edge is so inclined as to come closer to a longitudinal centerline of the sanitary napkin rearwardly.

6. A sanitary napkin according to claim 3, wherein W1/L1 is equal to or greater than 0.7, where L1 represents a length from the second starting point to a front end of the linear side edge and W1 represents a width from second the starting point to the front end of the linear side edge.

7. A sanitary napkin according to claim 1, wherein the skin-side surface of the main body has an elongated main absorbent region that is surrounded by a compressed groove and intended to face the wearer's body from the vaginal opening to the cleft of the buttocks, wherein
the main absorbent region has a rear end that is not spaced more than 20 mm apart longitudinally from the rear end of the leakage preventing wall.

8. A sanitary napkin according to claim 1, wherein when fully developed transversely outward, the sheet of the leakage preventing wall has a maximum width of 20 to 50 mm from the rising base.

9. A sanitary napkin according to claim 1, which has a length equal to or greater than 400 mm and a width equal to or greater than 180 mm between the linear side edges of the rear flaps.

10. A sanitary napkin according to claim 1, wherein the leakage preventing wall is accordion-folded at two fold lines, the accordion-folded wall being operable to unfold obliquely upward to upwardly extend a skin-contacting panel of the leakage preventing wall.

11. A sanitary napkin according to claim 3, wherein the lateral distance from a longitudinal centerline of the sanitary napkin to the linear side edge of each one of the rear flaps is greater than a maximum distance from the longitudinal centerline to a side edge of a corresponding one of the front flaps.

* * * * *